United States Patent [19]

Baltz et al.

[11] Patent Number: 4,537,957
[45] Date of Patent: Aug. 27, 1985

[54] PROCESS FOR THE PRODUCTION OF MYCAMINOSYLTYLONOLIDE

[75] Inventors: Richard H. Baltz; Gene M. Wild, both of Indianapolis, Ind.; Eugene T. Seno, Norwich, England

[73] Assignee: Eli Lilly and Company, Indianapolis, Ind.

[21] Appl. No.: 503,986

[22] Filed: Jun. 13, 1983

Related U.S. Application Data

[62] Division of Ser. No. 260,961, May 6, 1981, Pat. No. 4,419,447, which is a division of Ser. No. 156,854, Jun. 12, 1980, Pat. No. 4,321,361.

[51] Int. Cl.$^3$ .................... C07H 17/08; C12P 19/62
[52] U.S. Cl. ........................................ 336/7.1; 435/75
[58] Field of Search ........................................ 536/7.1

[56] References Cited

U.S. PATENT DOCUMENTS

| | | | |
|---|---|---|---|
| 3,178,341 | 4/1965 | Hamill et al. | 167/65 |
| 3,326,759 | 6/1967 | Hamill et al. | 167/65 |
| 3,344,024 | 9/1967 | Whaley et al. | 167/65 |
| 3,459,853 | 8/1969 | Gorman et al. | 424/121 |
| 4,056,616 | 11/1977 | Reimann et al. | 424/180 |
| 4,161,523 | 7/1979 | Weinstein et al. | 424/181 |
| 4,196,280 | 4/1980 | Umezawa et al. | 536/17 R |
| 4,205,163 | 5/1980 | Mori et al. | 536/17 R |

OTHER PUBLICATIONS

Kinumaki et al., "Macrolide Antibiotics M-4365 Produced by Micromonospora II, *J. Antibiotics*, 30 (6), 450–454, (1977).
Tanabe Pharmaceutical, Derwent Abstract 86252X/46 of Japanese Examined Patent 6037-351.
Yamaguchi et al., "Macrolide Antibiotics M-4365 Produced by Micromonospora III, In Vitro Antimicrobial Activity of Antibiotic M-4365G$_2$ (De-epoxy Rosamicin)", *J. Antibiotics*, 31 (5), 433–440, (1973).
Tsukiura et al., "Studies on Cirramycin A$_1$, III, Structure of Cirramycin A$_1$", *J. Antibiotics*, 22 (3), 89–99, (1969).
Nash et al., "A6888, A New Macrolide Complex Related to the Cirramycins", Current Chemotherapy and Infectious Disease Proceedings of 11th ICC and the 19th ICAAC, American Society of Microbiology, pp. 462–463, (1980).
Masamune et al., "Tylonolide Hemiacetal, the Aglycone of Tylosin and its Partial Synthesis", *J. Amer. Chem. Soc.* 98 (24) 7874–7875, (1976).
Okamoto et al., "Abstract from *Chem. Abstr.* 93: 68863u, (1980), of Japanese Kokai Tokkyo Koho 80 43,0183.

*Primary Examiner*—Johnnie R. Brown
*Assistant Examiner*—Elli Peselev
*Attorney, Agent, or Firm*—Nancy J. Harrison; Arthur R. Whale

[57] ABSTRACT

23-Demycinosyltylosin (DMT) which has the formula:

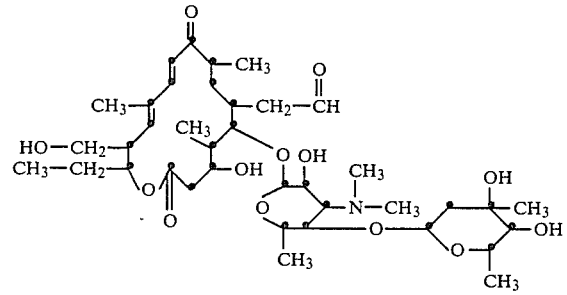

20-dihydro-DMT, specified acyl ester derivatives, and their acid addition salts are useful antibacterial agents. Improved methods of making 5-O-mycaminosyltylonolide (OMT) and 20-dihydro-OMT by mild acid hydrolysis of DMT and 20-dihydro-DMT, respectively, are included.

4 Claims, 1 Drawing Figure

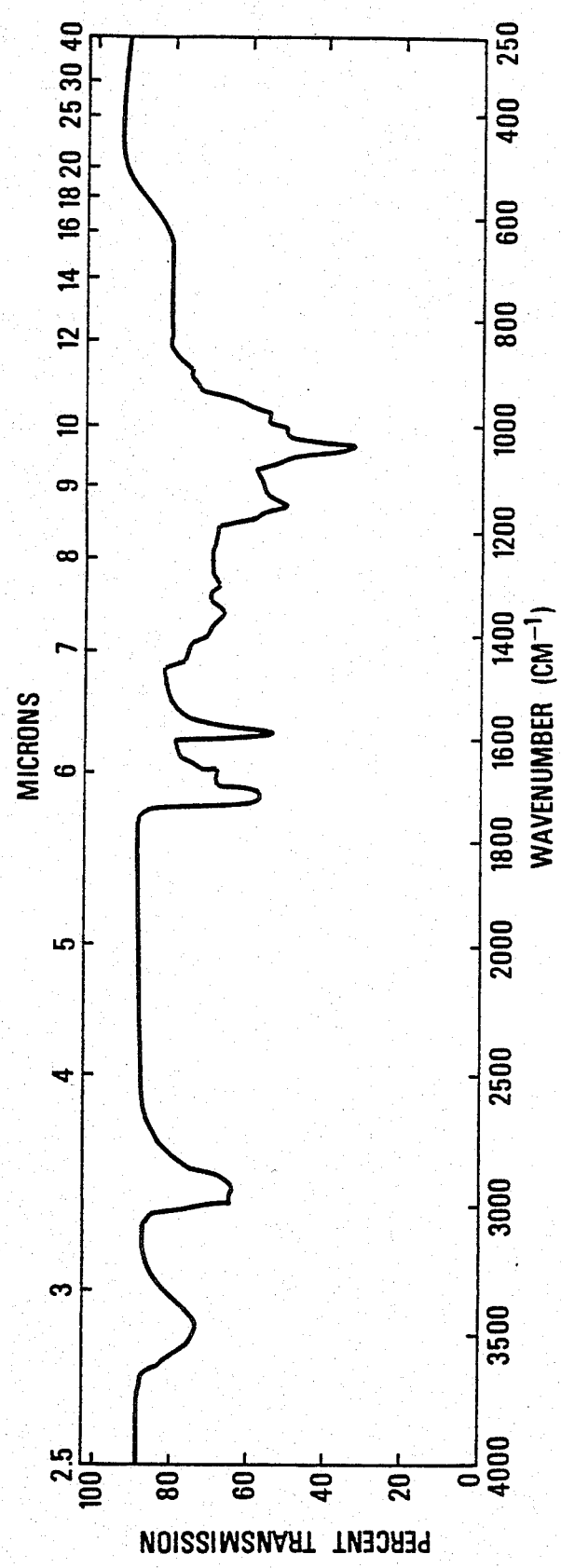

PROCESS FOR THE PRODUCTION OF MYCAMINOSYLTYLONOLIDE

This application is a division of application Ser. No. 260,961 filed May 6, 1981, now U.S. Pat. No. 4,419,447, which in turn is a division of application Ser. No. 156,854, filed on June 12, 1980, which issued as U.S. Pat. No. 4,321,361 on Mar. 23, 1982.

SUMMARY OF THE INVENTION

This invention relates to 23-demycinosyltylosin, a new macrolide antibiotic, and to its 20-dihydro derivative. 23-Demycinosyltylosin which will be called demycinosyltylosin or DMT for convenience herein has structure 1:

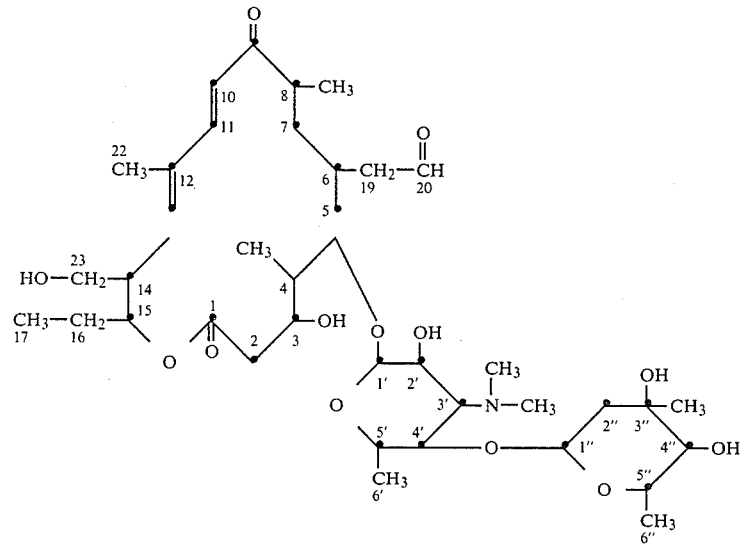

Although no stereochemical assignments are indicated in the structures given herein, the stereochemistry of the compounds is identical to that of tylosin. The neutral sugar in structure 1 is mycarose, and the aminosugar in 1 is mycaminose.

The dihydro-derivative of DMT, i.e. 20-dihydro-23-demycinosyltylosin will be called dihydro-DMT for convenience herein. Dihydro-DMT has structure 2:

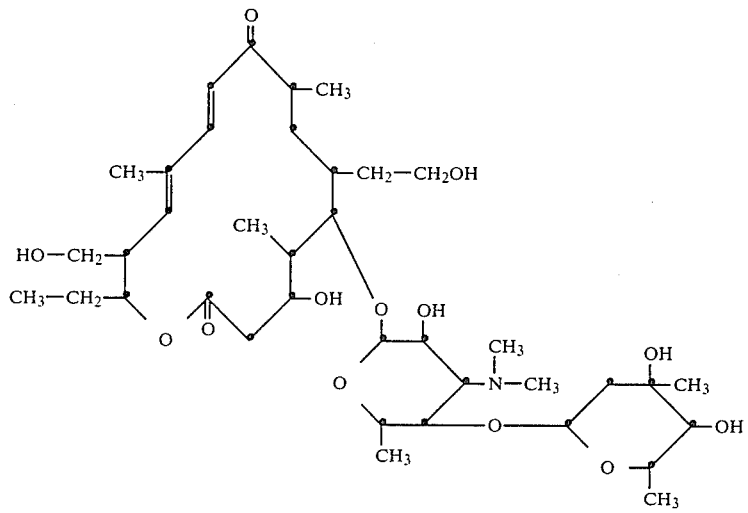

DMT and dihydro-DMT inhibit the growth of organisms which are pathogenic to animals. More specifically, DMT and dihydro-DMT are antibacterial agents which are especially active against gram-positive microorganisms and Mycoplasma species.

The hydroxyl groups of DMT and dihydro-DMT can be esterified on the 2', 4", 3", 23 and 3-hydroxyl groups to form useful acyl ester derivatives. In addition, dihydro-DMT can be esterified on the 20-hydroxyl group. Esterification of the 2'-hydroxyl group is most facile. Typical esters are those of a monocarboxylic acid or hemi-esters of a dicarboxylic acid having from 2 to 18 carbon atoms.

DMT, dihydro-DMT and their acyl ester derivatives are basic compounds which, when treated with acids, are converted to acid addition salts. These addition salts are also part of this invention. To simplify discussions of utility, the term "DMT compound" is used and refers to DMT, dihydro-DMT, a specified acyl ester derivative of these compounds, or a pharmaceutically acceptable acid addition salt of DMT, dihydro-DMT or of their acyl ester derivatives.

This invention further relates to a new strain of *Streptomyces fradiae*, NRRL 12170, and to the method of producing DMT or dihydro-DMT by culturing this strain under submerged aerobic fermentation conditions until a substantial level of antibiotic activity is produced. DMT or dihydro-DMT can be extracted from basified broth filtrate with polar organic solvents, and can be further purified by extraction, adsorption and/or crystallization.

This invention also relates to improved methods of preparing 5-O-mycaminosyltylonolide (OMT) and 20-dihydro-5-O-mycaminosyltylonolide (dihydro-OMT) by mild acid hydrolysis of DMT and dihydro-DMT, respectively.

DESCRIPTION OF THE DRAWING

The infrared absorption spectrum of DMT (free base) in chloroform is presented in the accompanying drawing.

DETAILED DESCRIPTION

DMT

The following paragraphs describe the properties of DMT. The structure of DMT is shown in formula 1.

DMT is a white solid which crystallizes from aqueous acetone. DMT softens at about 132° and slowly melts up to about 150° C. Elemental analysis of DMT indicates that it has the following approximate percentage composition: carbon, 61%; hydrogen, 8.5%; nitrogen, 2%; oxygen, 28%. DMT has an empirical formula of $C_{38}H_{63}NO_{13}$ and a molecular weight of about 742 (741 as determined by mass spectrometry).

The infrared absorption spectrum of DMT free base in chloroform is shown in the accompanying drawing. Observable absorption maxima occur at the following frequencies ($cm^{-1}$): 3634 (v. small), 3559 (shoulder), 3423 (broad), 2955 (intense), 2907 (intense), 1710 (intense), 1676 (shoulder), 1588 (intense), 1447 (shoulder), 1396 (shoulder), 1359 (small), 1309 (v. small), 1178 (shoulder), 1156 (intense), 1111 (shoulder), 1072 (shoulder), 1048 (intense), 1013 (shoulder), 984 (shoulder), 926 (v. small), 898 (v. small), and 833 (v. small).

The ultraviolet absorption spectrum of DMT in neutral ethanol exhibits an absorption maximum at 283 nm ($\epsilon 22,296$; $E_1\,_{cm}^{1\%}=300.9$).

DMT (free base) has the following specific rotation: $[\alpha]_D^{25}-53.5°$ (c 1, $CH_3OH$).

Electrometric titration of DMT in 66% aqueous dimethylformamide indicates the presence of a titratable group with a $pK_a$ value of about 7.25.

DMT base is soluble in water and in most polar organic solvents, such as acetone, methanol, ethanol, chloroform, dimethylformamide and dimethyl sulfoxide. DMT acid addition salts are more soluble in water than is DMT base.

DMT can be distinguished from tylosin and other known tylosin factors by paper and thin-layer chromatography. The approximate Rf and Rx values of DMT and various other tylosin factors are summarized in Tables 1 and 2. In Table 2 Rx value is the ratio of movement expressed relative to that of tylosin, which was given a value of 1.0. Bioautography with *Bacillus subtilis* was used for detection.

TABLE 1

| Thin-Layer Chromatography of DMT[a] | | | |
|---|---|---|---|
| | Rf Value | | |
| Compound | A[b] | B | C |
| Tylosin | 0.53 | 0.53 | 0.67 |
| DMT | 0.45 | 0.52 | 0.61 |
| Desmycosin | 0.47 | 0.24 | 0.17 |
| Macrocin | 0.23 | 0.49 | 0.60 |
| Relomycin | 0.34 | 0.51 | 0.63 |

[a]Medium: Merck, Darmstadt - Silica Gel 60
[b]Solvent:
A = ethyl acetate:diethylamine (96:4)
B = acetone:ethanol (2:1)
C = chloroform:methanol (3:1)

TABLE 2

| Paper Chromatography of DMT | | |
|---|---|---|
| | Rx | |
| Compound | D[b] | E |
| Tylosin | 1.0 | 1.0 |
| DMT | 0.76 | 0.95 |
| Desmycosin | 0.22 | 0.83 |
| Macrocin | 0.43 | 0.87 |
| Relomycin | 0.63 | 1.0 |

[a]Paper: Whatman No. 1 treated with 0.75 M $KH_2PO_4$ buffer at pH 4.0 and dried
[b]Solvent:
D = ethyl acetate saturated with water
E = n-butanol saturated with water

DIHYDRO-DMT

The dihydro derivative of DMT can be obtained by chemical reduction or by fermentation. When preparing dihydro-DMT by chemical reduction, known procedures such as, for example, treating DMT with an approximately stoichiometric amount of sodium borohydride in an alcoholic solvent, may be used. Dihydro-DMT is also produced by the *S. fradiae* NRRL 12170 of this invention under controlled fermentation conditions.

ESTER DERIVATIVES

DMT and dihydro-DMT can be esterified at the 2', 4", 3", 23 and 3-positions to give acyl ester derivatives by treatment with acylating agents using methods known in the art. In addition, dihydro-DMT can be esterified at the 20-position. Esterification of the 2'-hydroxyl group is most facile. Typical acylating agents include anhydrides, halides (usually in combination with a base or other acid scavenger) and active esters of organic acids. Acylation can also be achieved by using a mixture of an organic acid and a dehydrating agent such as N,N'-dicyclohexylcarbodiimide. Acylations can also be carried out enzymatically as described by Okamoto et al. in U.S. Pat. No. 4,092,473. Once formed, the acyl derivatives can be separated and purified by known techniques.

The 2'-monoester derivatives can be prepared by selective esterification techniques generally known in the art, such as, for example, treatment of the antibiotic with a stoichiometric quantity (or a slight excess) of an acylating agent, such as an acyl anhydride, at about room temperature for from about 1 to about 24 hours until esterification is substantially complete. The 2'-monoester can be isolated from the reaction mixture by standard procedures such as extraction and chromatography and crystallization.

Useful esters are those of organic acids including aliphatic, cycloaliphatic, aryl, aralkyl, heterocyclic carboxylic, sulfonic and alkoxycarbonic acids of from 2 to 18 carbon atoms, and of inorganic acids, such as sulfuric and phosphoric acids.

Representative suitable esters include those derived from acids such as acetic, chloroacetic, propionic, butyric, isovaleric, alkoxycarbonic, stearic, cyclopropanecarboxylic, cyclohexanecarboxylic, β-cyclohexylpropionic, 1-adamantanecarboxylic, benzoic, phenylacetic, phenoxyacetic, mandelic and 2-thienylacetic acids, and alkyl-, aryl-, and aralkyl-sulfonic acids, the aryl- and aralkyl- acids optionally bearing substituents such as halogen, nitro, lower alkoxy and the like on the aromatic moiety. Suitable esters also include hemi-esters derived from dicarboxylic acids such as succinic, maleic, fumaric, malonic and phthalic acids.

Pharmaceutically acceptable ester derivatives are a preferred group. Other ester derivatives are useful, however, as intermediates.

SALTS

DMT, dihydro-DMT and their specified derivatives form acid addition salts. The acid addition salts of DMT, dihydro-DMT and of their acyl derivatives are also part of this invention. Such salts are useful, for example, for separating, purifying and crystallizing DMT, dihydro-DMT and their acyl derivatives. In addition, the salts have an improved solubility in water.

Representative suitable salts include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicyclic, methanesulfonic, benzenesulfonic, sorbic, picric, benzoic, cinnamic and the like acids.

Pharmaceutically acceptable acid addition salts are an especially preferred group of salts of this invention. "Pharmaceutically acceptable" salts are salts in which the toxicity of the compounds as a whole toward warm-blooded animals is not increased relative to the non-salt form.

PREPARATION OF OMT AND DIHYDRO-OMT

This invention also relates to improved methods of preparing OMT and dihydro-OMT by mild acid hydrolysis of DMT and dihydro-DMT, respectively. Mild acid hydrolysis conditions are known in the art. Appropriate solutions having a pH of about four or below can be used to accomplish the hydrolysis. Temperatures of about 20° to about 100° C. can be used in this method. The reaction time needed to carry out the hydrolysis varies, depending upon the pH of the reaction mixture and the temperature used. At higher pH levels the reaction rate is slower, and at higher temperatures the reaction rate is faster. The reaction is carried out by treating either DMT or dihydro-DMT with a mild acid solution for a time sufficient to effect removal of the mycarosyl group to give OMT or dihydro-OMT, respectively.

Alternatively, and sometimes preferably, OMT or dihydro-OMT can be prepared by treating DMT of dihydro-DMT in the fermentation broth in which it is produced, using mild acidic conditions as above described for a time sufficient to convert the DMT or dihydro-DMT to OMT or dihydro-OMT, respectively. OMT or dihydro-OMT thus prepared can be isolated from the fermentation broth using techniques known in the art.

OMT and dihydro-OMT are described by Gorman et al. in U.S. Pat. No. 3,459,853. In U.S. Pat. No. 3,459,853 OMT and dihydro-OMT are prepared by controlled acid hydrolysis of tylosin, desmycosin, macrocin, and lactenocin and their dihydro-derivatives. The art method of preparation involves removal of all the neutral sugars from tylosin, desmycosin, macrocin, or lactenocin to obtain OMT. Analogous methods are taught to prepare dihydro-OMT. Removal of the neutral sugar at the 23-position requires conditions which result in marked product losses. The process of this invention avoids such losses.

PREPARATION OF DMT AND DIHYDRO-DMT BY *S. FRADIAE*

DMT and dihydro-DMT are prepared by culturing a strain of *Streptomyces fradiae* which produces these compounds under submerged aerobic conditions in a suitable culture medium until substantial antibiotic activity is produced. As will be appreciated by those skilled in the art, DMT is produced first in the fermentation process. Dihydro-DMT is produced when the fermentation is carried out for a longer time, thus permitting the DMT present to be reduced enzymatically.

The culture medium used to grow *Streptomyces fradiae* NRRL 12170 can be any one of a number of media. For economy in production, optimal yield, and ease of product isolation, however, certain culture media are preferred. Thus, for example, preferred carbon sources in large-scale fermentation include carbohydrates such as dextrin, glucose, starch, and corn meal, and oils such as soybean oil. Preferred nitrogen sources include corn meal, soybean meal, fish meal, amino acids and the like. Among the nutrient inorganic salts which can be incorporated in the culture media are the customary soluble salts capable of yielding iron, potassium, sodium, magnesium, calcium, ammonium, chloride, carbonate, sulfate, nitrate, and like ions.

Essential trace elements necessary for the growth and development of the organism should also be included in the culture medium. Such trace elements commonly occur as impurities in other constituents of the medium in amounts sufficient to meet the growth requirements of the organism. It may be necessary to add small amounts (i.e. 0.2 ml/L) of an antifoam agent such as polypropylene glycol (M.W. about 2000) to large-scale fermentation media if foaming becomes a problem.

For production of substantial quantities of DMT or dihydro-DMT, submerged aerobic fermentation in tanks is preferred. Small quantities of DMT or dihydro-DMT may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form of mycelial fragments of the organism to obtain a fresh, actively growing culture of the organism. The vegetative inoculum is then transferred to a larger tank. The medium used for the vegetative inoculum can be the same as that used for larger fermentations, but other media can also be used.

*S. fradiae* NRRL 12170 can be grown at temperatures between about 10° and about 37° C. Optimum antibiotic production appears to occur at temperatures of about 28° C.

As is customary in aerobic submerged culture processes, sterile air is bubbled through the culture medium. For efficient antibiotic production the percent of air saturation for tank production should be about 30% or above (at 28° C. and one atmosphere of pressure).

Antibiotic production can be followed during the fermentation by testing samples of the broth against organisms known to be sensitive to these antibiotics. One useful assay organism is *Staphylococcus aureus* ATCC 9144. The bioassay is conveniently performed by an automated turbidometric method. In addition, antibiotic production can be readily monitored by high-performance liquid chromatography with UV detection.

Following its production under submerged aerobic fermentation conditions, DMT or dihydro-DMT can be recovered from the fermentation medium by methods used in the fermentation art. Recovery of DMT or dihydro-DMT is accomplished by an initial filtration of the fermentation broth. The filtered broth can then be further purified to give the desired antibiotic. A variety of techniques may be used in this purification. A preferred technique for purification of the filtered broth involves adjusting the broth to about pH 9; extracting the broth with a suitable solvent such as ethyl acetate, amyl acetate, or methyl isobutyl ketone; extracting the organic phase with an aqueous acidic solution, and precipitating the antibiotic by making the aqueous extract basic. Further purification involves the use of extraction, adsorption and/or precipitation techniques.

THE MICROORGANISM

The new microorganism of this invention was obtained by chemical mutagenesis of a *Streptomyces fradiae* strain which produced tylosin. The microorganism obtained by mutagenesis produces only minimal amounts of tylosin, but produces DMT as a major component.

For characterization purposes, the new organism was compared with *Streptomyces fradiae* strain M48-E 2724.1, a tylosin-producing strain derived from *S. fradiae* NRRL 2702. *S. fradiae* NRRL 2702 was disclosed by Hamill et al. in U.S. Pat. No. 3,178,341, issued Apr. 13, 1965. In the discussions herein the tylosin-producing *S. fradiae* M48-E 2724.1 culture will be called "E2724.1".

The new DMT- and dihydro-DMT-producing strain NRRL 12170 is is also classified as a strain of *Streptomyces fradiae*. In characterizing this organism, the methods recommended for the International Streptomyces Project for the characterization of Streptomyces species have been followed [E. B. Shirling and D. Gottlieb, "Methods For Characterization of Streptomyces Species," *Internal. Journal of Systematic Bacteriology*, 16 (3), 313–340 (1966)] along with certain supplementary tests. The following references to *S. fradiae* in the literature were consulted: (1) R. E. Buchanan and N. E. Gibbons, "Bergey's Manual of Determinative Bacteriology," 8th ed., The Williams and Wilkins Co., Baltimore, Md., 1974, p. 815; and (2) E. B. Shirling and D. Gottlieb, "Cooperative Description of Streptomyces. II. Species Description from First Study," *Internal. Journal of Systematic Bacteriology*, 18 (2), 118, (1968).

The following description of the DMT-producing strain compares its characteristics with those of the tylosin-producing *S. fradiae* strain "E2724.1".

CHARACTERIZATION OF THE MICROORGANISM

The spore-chain morphology of the new strain and of the E2724.1 strain is in the Retinaculum-Apertum (RA) section. Hooks, loops, and irregular coils are short and generally not of a wide diameter. This is best observed on ISP#2 (yeast-malt extract agar). The spore surface is smooth; the spore shape is spherical with an average size of 0.65 $\mu$M in diameter. The diameter range is from 0.61 to 0.71 $\mu$M.

The most obvious differences between these strains are seen in their cultural characteristics. The E2724.1 strain produces aerial mycelia fairly well on most media and is in the White color series. The DMT-producing strain produces very little if any aerial mycelia. When present, it is in the White to Gray color series. The reverse sides of these colonies have no distinctive pigments produced. They are light to moderate yellow in color. Melanoid pigment production is negative[1].

[1]Melanoid-pigment production was tested using ISP#1 (tryptone-yeast extract broth), ISP#6 (peptone yeast extract-iron agar), ISP#7 (tyrosine agar), and ISP#7 agar without tyrosine.

A summary of the important similarities and differences between the E2724.1 strain and the DMT-producing strain is given in Table 3.

TABLE 3

| Comparison of *Streptomyces fradiae* E2724.1 and NRRL 12170 | |
|---|---|
| Similarities | Differences |
| Spore-chain morphology | Cultural characteristics |
| Spore-surface ornamentation | Carbon utilization |
| Spore size | Gelatin liquefaction |
| Lack of chromogenicity | NaCl tolerance |
| Lack of soluble pigments | pH range |
| Growth in selected vegetative media | Temperature range |
| Starch hydrolysis | |
| Negative skim milk reaction | |
| Nitrate reduction | |
| Catalase positive | |
| Phosphatase positive | |
| Urease negative | |
| Antibiotic sensitivity pattern | |

The morphology and growth characteristics of the *S. fradiae* E2724.1 and NRRL 12170 strains are compared in Table 4. In the tables which follow the antibiotic sensitivities (Table 5), carbon utilization (Table 6) and miscellaneous physiological characteristics (Table 7) are compared.

TABLE 4

| Growth Characteristics and Morphology | | | |
|---|---|---|---|
| | | E2724.1 | NRRL 12170 |
| Sporophores | | RA | RA |
| Spore chains | | >10 | >10 |
| Spore surface[1] | | smooth | smooth |
| Spore shape | | spherical | spherical |
| ISP#2 | G[2] | good | good |
| | R | 87. m. yellow[3] | 87. m. yellow |
| | Am | good 263. white | fair 263. white |
| | Sp | none | none |
| ISP#3 | G | poor | poor |
| | R | 263. white | 263. white |
| | Am | poor 263. white | trace |
| | Sp | none | none |
| ISP#4 | G | abundant | good |
| | R | 87. m. yellow | 87. m. yellow |
| | Am | abundant 263. white | poor |
| | Sp | none | none |
| ISP#5 | G | good | good |
| | R | 86.1. yellow | 86.1 yellow |
| | Am | good 92. y. white | none |

TABLE 4-continued

Growth Characteristics and Morphology

| | | E2724.1 | NRRL 12170 |
|---|---|---|---|
| ISP#7 | Sp | none | none |
| | G | abundant | good |
| | R | 87. m. yellow | 87. m. yellow |
| | Am | abundant 263. white | fair 265. med. gray |
| Bennett's | Sp | none | light brown |
| | G | poor | no growth |
| | R | 90. gy. yellow | — |
| | Am | none | — |
| | Sp | none | — |
| Ca—malate | G | good | poor |
| | R | 263. white | 92. y. white |
| | Am | good 263. white | none |
| | Sp | none | none |
| Czapek's | G | good | fair |
| | R | 87. m. yellow | 87. m. yellow |
| | Am | abundant 263. white | trace |
| | Sp | none | none |
| Glucose-asparagine | G | no growth | no growth |
| | R | — | — |
| | Am | — | — |
| | Sp | — | — |
| Tomato paste-oatmeal | G | abundant | good |
| | R | 92. y. white | 87. m. yellow |
| | Am | abundant 263. white | none |
| | Sp | none | none |

[1]Spore-surface ornamentation was determined using a scanning electron microscope.
[2]G = Growth; R = Reverse or underside of colony; Am = Aerial mycelium; Sp = soluble pigment
[3]Color names were assigned using the ISCC-NBS color charts (K. L. Kelly and D. B. Judd, "The ISCC-NBS Centroid Color Charts Standard Sample No. 2106," U.S. Dept. of Commerce, National Bureau of Standards, Washington, D.C. 20234)

TABLE 5

Antibiotic Sensitivity[a,b]

| Antibiotic | Conc. | Class Compound | E2724.1 | NRRL 12170 |
|---|---|---|---|---|
| Chloramphenicol | 30 μg | nitrophenyl compound | + | + |
| Erythromycin | 15 μg | macrolide | tr | tr |
| Cephaloridine | 30 μg | β-lactam | + | + |
| Lincomycin | 2 μg | lincosaminide | — | — |
| Polymyxin B | 300 units | peptide | tr | tr |
| Streptomycin | 10 μg | aminoglycoside | + | + |
| Tetracycline | 30 μg | tetracycline | + | + |
| Vancomycin | 30 μg | glycopeptide | + | + |

[a]Determined by using sensitivity discs padded onto seeded-agar plates.
[b]— = resistance (no zones of inhibition)
+ = sensitivity (zones of inhibition)
tr = trace of sensitivity

TABLE 6

Carbon Utilization[a,b]

| Carbon Source | E2724.1 | NRRL 12170 |
|---|---|---|
| Control: no carbon | — | — |
| Control: Glucose | + | + |
| L-Arabinose | — | + |
| D-Fructose | + | + |
| D-Galactose | + | + |
| i-Inositol | + | + |
| D-Mannitol | — | + |
| Raffinose | — | — |
| Salicin | — | — |
| Sucrose | + | + |
| D-Xylose | + | + |
| D-Rhamnose | — | + |

[a]— = no utilization
+ = utilization
[b]Determined on International Streptomyces Project (ISP)#9 (carbon-utilization agar) basal medium to which filter-sterilized carbon sources were added to equal a final concentration of 1.0%. Plates were incubated at 30° C. and observed after 7 and 12 days. 3-(N—morpholino)propanesulfonic acid, pH 7; N—2-hydroxyethylpiperazine-N'—2-ethanesulfonic acid, pH 8; 2-amino-2-(hydroxymethyl)-1,3-propane-diol, pH 9; 3-cyclohexylamino-1,1-propanesulfonic acid, pH 10, 11. The pH of the agar after seven days' incubation was taken as the correct value since some of the buffers failed to hold their adjusted pH. Buffer toxicity was tested by adjusting all the buffers to pH 7.0 and determining growth. No toxicity was noted.
[3]Tested at 5, 10, 15, 20, 25, 30, 37, 40, 45, 50 and 55° C.
[4]Measured by adding NaCl to the agar to equal: 0, 2, 4, 6, 8, 10 and 12% NaCl by weight
[5]Starch hydrolysis was determined by testing for the presence of starch with iodine on ISP#4 (inorganic salts-starch agar) plates
[6]The methods of Blazevic and Ederer were followed for the enzyme assays (D. J. Blazevic and G. M. Ederer, "Principles of Biochemical Tests in Diagnostic Microbiology," John Wiley and Sons, New York, N.Y., 1975).

TABLE 7

Miscellaneous Physiological Characteristics

| | E2724.1 | NRRL 12170 |
|---|---|---|
| ISP#1 (chromogenicity) | — | — |
| ISP#6 (chromogenicity) | — | — |
| ISP#7 (chromogenicity) | — | — |
| Gelatin liquefaction | — | + |
| Skim-milk reaction | — | — |
| pH growth range[1,2] | 6.1–8.8 | 6.1–7.8 |
| Temperature growth range[1,3] | 10–37° C. | 10–30° C. |
| NaCl tolerance[1,4] | 8% | 4% |
| Starch hydrolysis[5] | + | + |
| Nitrate reduction | + | + |
| Catalase[6] | + | + |
| Phosphatase[6] | + | + |
| Urease[6] | — | — |

[1]On ISP#2 (yeast extract-malt extract agar) medium; incubated 7 days
[2]Determined using the following buffers at a concentration of 0.05 M: citric acid, pH 3, 4, 5; 2-(N—morpholino)ethanesulfonic acid, pH 6;

Based on the foregoing characteristics the DMT- and dihydro-DMT-producing organism, NRRL 12170, is classified as a new strain of *Streptomyces fradiae*. This culture has been deposited and made part of the stock culture collection of the Northern Regional Research Center, Agricultural Research, North Central Region, 1815 North University Street, Peoria, Ill., 61604, from which it is available to the public under the accession number NRRL 12170.

As is the case with other organisms, the characteristics of *Streptomyces fradiae* NRRL 11270 are subject to variation. For example, artificial variants and mutants of the NRRL 12170 strain may be obtained by treatment with various known physical and chemical mutagens, such as ultraviolet rays, X-rays, gamma rays, and N-methyl-N'-nitro-N-nitrosoguanidine. All natural and artificial variants, mutants and recombinants of *Streptomyces fradiae* NRRL 12170 which retain the characteristic of production of DMT may be used in this invention.

ACTIVITY OF DMT COMPOUNDS

The DMT compounds inhibit the growth of pathogenic bacteria, especially gram-positive bacteria and Mycoplasma species. Table 8 summarizes the minimal inhibitory concentrations (MIC), as measured by standard agar-dilution assays, at which DMT (free base) inhibits certain bacteria.

TABLE 8

In Vitro Activity of DMT Free Base

| Organism | MIC (μg/ml) |
|---|---|
| *Streptococcus pyogenes* C203 | 0.25 |
| *Streptococcus pneumoniae* Park I | 0.13 |
| Streptococcus sp. (Group D) 282 | 0.5 |
| *Staphylococcus aureus* 3055 | 1.0 |
| *Staphylococcus aureus* 209P | 0.25 |
| *Pasteurella multocida* | 3.12 |
| *Pasteurella hemolytica* | 12.5 |
| *Mycoplasma gallisepticum* | 0.097 |
| *Mycoplasma hyopneumoniae* | 0.195 |
| *Mycoplasma hyorhinis* | 0.78 |

The DMT compounds have shown in vivo antimicrobial activity against experimental bacterial infections. When two doses of test compound were administered to mice in experimental infections, the activity observed was measured as an $ED_{50}$ value [effective dose in mg/kg to protect 50% of the test animals: see Warren Wick, et al., *J. Bacteriol.* 81, 233–235 (1961)]. The $ED_{50}$ values observed for DMT and DMT tartrate were given in Table 9.

TABLE 9

Subcutaneous and Oral $ED_{50}$ Values (mg/kg × 2)

| Compound | *Streptococcus pyogenes* C203 Subcut. | *Streptococcus pyogenes* C203 Oral | *Streptococcus pneumoniae* Park I Subcut. | *Streptococcus pneumoniae* Park I Oral | *Staphylococcus aureus* 3055 Subcut. | *Staphylococcus aureus* 3055 Oral |
|---|---|---|---|---|---|---|
| DMT Base | 2.2 | 218 | 15.7 | 66 | 2.7 | 64 |
| DMT Tartrate | 2.3 | 172 | ≦9.9 | 100 | NT* | NT |
| Bacterial Challenge (× $LD_{50}$) | 13 | 11.3 | 3 | 2.7 | 21 | 26 |

*not tested

Activity against Mycoplasma species is an especially useful aspect of the DMT compounds. Tables 10 and 11 summarize experiments using DMT and DMT tartrate for the treatment of induced *Mycoplasma gallisepticum* infections in chickens. The compounds were administered in the drinking water (at 1 and 2 grams per gallon for 1 to 3 days) or by injection at 15 or 30 mg/kg of body weight.

TABLE 10

TREATMENT OF INDUCED *MYCOPLASMA GALLISEPTICUM* INFECTION IN CHICKS WITH DMT BASE

| Compound | Dosage | No. Died/Total No. | No. with Air Sac Lesions/Total No. | Avg. Wt. (g) | No. with *M. gallisepticum* Antibody/Total No. |
|---|---|---|---|---|---|
| DMT Base | 2.0 g/gal; 1–3 days | 9/30 (30%) | 26/30 (86.7%) | 397 | 21/21 (100%) |
| DMT Base | 1.0 g/gal; 1–3 days | 13/30 (43.3%) | 28/30 (93.3%) | 392 | 15/17 (88.2%) |
| DMT Base | 15 mg/kg | 10/30 (33.3%) | 24/30 (80%) | 453 | 20/20 (100%) |
| Infected Control | — | 19/30 (63%) | 30/30 (100%) | 304 | 11/11 (100%) |

TABLE 11

TREATMENT OF INDUCED *MYCOPLASMA GALLISEPTICUM* INFECTION IN CHICKS WITH DMT TARTRATE

| Compound | Dosage | No. Died/Total No. | No. with Air Sac Lesions/Total No. | Avg. Wt. (g) | No. with *M. gallisepticum* Antibody/Total No. |
|---|---|---|---|---|---|
| DMT Tartrate | 2.0 g/gal; 1–3 days | 0/30 (0%) | 13/30 (43.3%) | 458 | 17/30 (56.7%) |
| DMT Tartrate | 1.0 g/gal; 1–3 days | 2/30 (6.7%) | 22/29 (75.9%) | 354 | 27/28 (96.4%) |
| DMT Tartrate | 30 mg/kg | 10/30 (33.3%) | 27/30 (90%) | 330 | 16/20 (80%) |
| Infected Control | — | 15/30 (50%) | 30/30 (100%) | 231 | 15/15 (100%) |

For the prevention or treatment of Mycoplasma infections in poultry, a non-toxic amount of a DMT compound is administered to birds orally or parenterally. DMT compounds are most conveniently administered with a pharmaceutically acceptable carrier, such as the water ingested by the birds.

Studies on the acute toxicity of DMT are summarized in Table 12. In these studies, 4- to 5-week-old Harlan ICR mice were used. The median lethal dose ($LD_{50}$) was determined for DMT by the oral (p.o.), subcutaneous (s.c.), intravenous (i.v.), and intraperitoneal (i.p.) routes of administration.

TABLE 12

Acute Toxicity of DMT

| Route | $LD_{50}$ (mg/kg) Males | $LD_{50}$ (mg/kg) Females |
|---|---|---|
| p.o. | — | >5000 |
| s.c. | — | 5447 |
| i.v. | 100 | 186 |
| i.p. | 721 | 325 |

In order to illustrate more fully the operation of this invention, the following examples are provided:

EXAMPLE 1

A. Shake-flask Fermentation of DMT

A lyophilized pellet of *Streptomyces fradiae* NRRL 12170 is dispersed in 1–2 ml of sterilized water. A portion of this solution (0.5 ml) is used to inoculate a vegetative medium (150 ml) having the following composition:

| Ingredient | Amount (%) |
|---|---|
| Corn steep liquor | 1.0 |
| Yeast extract | 0.5 |
| Soybean grits | 0.5 |

-continued

| Ingredient | Amount (%) |
|---|---|
| CaCO₃ | 0.3 |
| Soybean oil (crude) | 0.45 |
| Deionized water | 97.25 |

Alternatively, a vegetative culture of *S. fradiae* NRRL 12170 preserved, in 1-ml volumes, in liquid nitrogen is rapidly thawed and used to inoculate the vegetative medium. The inoculated vegetative medium is incubated in a 500-ml Erlenmeyer flask at 29° C. for about 48 hours on a closed-box shaker at 300 rpm.

This incubated vegetative medium (0.5 ml) is used to inoculate 7 ml of a production medium having the following composition:

| Ingredient | Amount (%) |
|---|---|
| Beet molasses | 2.0 |
| Corn meal | 1.5 |
| Fish meal | 0.9 |
| Corn gluten | 0.9 |
| NaCl 0.1 | 0.1 |
| (NH₄)₂HPO₄ | 0.04 |
| CaCO₃ | 0.2 |
| Soybean oil (crude) | 3.0 |
| Deionized water | 91.36 |

The inoculated fermentation medium is incubated in a 50-ml bottle at 29° C. for about 6 days on a closed-box shaker at 300 rpm.

B. Tank Fermentation of DMT

In order to provide a larger volume of inoculum, 1200 ml of incubated vegetative medium, prepared in a manner similar to that described in section A, is used to inoculate 250 gallons of a second-stage vegetative growth medium having the following composition:

| Ingredient | Amount (%) |
|---|---|
| Corn steep liquor | 1.0 |
| Soybean oil meal | 0.5 |
| Yeast extract | 0.5 |
| CaCO₃ | 0.3 |
| Soybean oil (crude) | 0.5 |
| Lecithin (crude) | 0.015 |
| Water | 97.185 |
| Adjust pH to 8.5 with 50% NaOH solution. | |

This second-stage vegetative medium is incubated in a 350-gallon tank for about 48 hours at 28° C., with adequate aeration and agitation.

Incubated second-stage medium (144 gallons) thus prepared is used to inoculate 1000 gallons of sterile production medium having the following composition:

| Ingredient | Amount (%) |
|---|---|
| Fish meal | 0.875 |
| Corn meal | 1.5 |
| Corn gluten | 0.875 |
| CaCO₃ | 0.2 |
| NaCl | 0.1 |
| (NH₄)₂HPO₄ | 0.04 |
| Beet molasses | 2.0 |
| Soybean oil (crude) | 3.0 |
| Lecithin | 0.09 |
| Water | 91.32 |
| Adjust pH to 7.2 with 50% NaOH solution. | |

The inoculated production medium is allowed to ferment in a 1600-gallon tank for 8 to 9 days at a temperature of 28° C. The fermentation medium is aerated with sterile air to keep the dissolved oxygen level between about 30% and 50% and is stirred with conventional agitators at about 250 rpm.

EXAMPLE 2

Isolation of DMT

Harvested whole broth (3800 L), obtained as described in Example 1, is filtered, using a filter aid. The mycelial cake is washed with water; this water wash is added to the filtrate.

The pH of the filtrate is adjusted to pH 9.2, using a 50% aqueous solution of sodium hydroxide (9.5 L). The filtrate is extracted with ethyl acetate (2,000 L). Deionized water (450 L) and sodium phosphate monobasic (6.4 kg) are added to the ethyl acetate extract. The resulting solution is thoroughly mixed. The pH of this solution is adjusted from about pH 6.0 to pH 4.35, using a phosphoric acid solution (3300 ml; 2 parts water to one part phosphoric acid). The aqueous phase is separated. The pH of the enriched aqueous phase is adjusted to pH 6.5 using a 50% aqueous sodium hydroxide solution (700 ml).

The resulting solution is concentrated to a volume of about 225 L under vacuum. The pH of the concentrated solution is adjusted to pH 9.2 by the addition of 10% aqueous sodium hydroxide (16 L). The resulting basic solution is permitted to stand overnight. The crystals which form are separated by filtration, washed with deionized water (50 L), and dried to give about 8.6 kg of product. A portion of the product thus obtained (3 kg) is recrystallized from acetone-water to give about 2.07 kg of DMT free base.

EXAMPLE 3

Preparation of OMT

DMT, prepared as described in Example 2, is dissolved in a dilute hydrochloric acid solution (HCl added to water until the pH of the solution is 1.8). The resulting solution is allowed to stand for 24 hours at room temperature and then is adjusted to pH 9.0 by the addition of sodium hydroxide. This basic solution is extracted with ethyl acetate, dichloromethane or chloroform. The extract is dried under vacuum to give OMT.

EXAMPLE 4

Preparation of Dihydro-DMT

DMT (50 mg), prepared as described in Example 2, is dissolved in an aqueous isopropyl alcohol solution (approximately 40%; 25 ml). Sodium borohydride (20 mg) is dissolved in a 30% aqueous isopropyl alcohol solution (10 ml). The NaBH₄ solution (1 ml) is added to the solution containing the DMT. The resulting mixture is stirred for 5 minutes, is adjusted to pH 7.5 with phosphoric acid, and is concentrated under vacuum to remove the isopropyl alcohol. Water is added to the resulting aqueous concentrate to give a volume of 25 ml; chloroform (50 ml) is added. The pH of the aqueous phase is adjusted to 7.5. After extraction, the chloroform is separated and evaporated to dryness under vacuum to give dihydro-DMT.

EXAMPLE 5

Preparation of Dihydro-OMT

Dihydro-DMT, prepared as described in Example 4, is treated in the manner described in Example 3 to give dihydro-OMT.

EXAMPLE 6

Alternative Preparation of OMT

OMT is prepared from DMT by treating the DMT in the fermentation broth in which it is produced with mild acid as described in Example 3. Isolation of the OMT is accomplished by a procedure similar to that described for DMT in Example 2.

EXAMPLE 7

2'-O-Propionyl-DMT

DMT is dissolved in acetone and treated with 1.2 equivalents of propionic anhydride at room temperature for about six hours to give 2'-O-propionyl-DMT.

EXAMPLES 8–10

2'-O-Isovalery-DMT, prepared according to the procedure of Example 7, but using isovaleric anhydride.

2'-O-Benzoyl-DMT, prepared according to the procedure of Example 7 but using benzoyl anhydride.

2'-O-(n-Butyryl)DMT, prepared according to the procedure of Example 7, but using n-butyric anhydride.

We claim:

1. The process for preparing 5-O-mycaminosyltylonolide which comprises treating 23-demycinosyltylosin at a temperature of about 20° C. to about 100° C. with a mild acid solution until 5-O-mycaminosyltylonolide is formed.

2. The process of claim 1 wherein the 23-demycinosyltylosin is present in the fermentation broth in which it is produced.

3. The process for of preparing 20-dihydro-5-O-mycaminosyltylonolide which comprises treating 20-dihydro-23-demycinosyltylosin at a temperature of about 20° C. to about 100° C. with a mild acid solution until 20-dihydro-5-O-mycaminosyltylonolide is formed.

4. The process of claim 3 wherein the 20-dihydro-23-demycinosyltylosin is present in the fermentation broth in which it is produced.

* * * * *